United States Patent [19]

Swinehart

[11] Patent Number: 5,863,546
[45] Date of Patent: Jan. 26, 1999

[54] COSMETIC COMPOSITION

[76] Inventor: James M Swinehart, 950 E. Harvard Ave., #630, Denver, Colo. 80210

[21] Appl. No.: 824,337

[22] Filed: Mar. 2, 1997

[51] Int. Cl.$^6$ ...................................................... A61N 7/48
[52] U.S. Cl. .............................. 424/401; 424/63; 424/64; 424/70.1; 514/557; 514/844; 514/845; 514/846; 514/859; 514/881
[58] Field of Search .................................... 424/401, 70.1, 424/63, 69; 514/880, 881, 557, 844, 845, 846, 847, 859

[56] References Cited

U.S. PATENT DOCUMENTS 4,917,891  4/1990  Kaufmann et al. ...................... 424/401
5,456,863  10/1995  Bermann ............................... 424/70.12

OTHER PUBLICATIONS

Fulton, (1989), *J. Soc. Cosmet. Chem.*, 40:321–333.

*Primary Examiner*—Jyothsna Venkat

[57] ABSTRACT

Methods for production of, and the ingredients of, a new and novel line of cosmetics that are simultaneously oil free, lanolin free, fragrance free, free of formaldehyde releasing preservatives, and with all ingredients rated "0" with respect to comedogenicity and irritancy in the published master list of comedogenic and irritating cosmetic ingredients are described. These formulations are thus hypoallergenic, noncomedogenic, nonacnegenic and aesthetically pleasing. The formulated cosmetic products include a moisture cream, moisture lotion, glycolic cream, glycolic lotion, shampoo, cleanser, colored makeup foundation, colored makeup powder, and colored makeup concealer.

24 Claims, No Drawings

COSMETIC COMPOSITION

BACKGROUND

1. Technical Field

This patent pertains to the field of cosmetics and skin care products, including moisture cream, moisture lotions, glycolic creams, glycolic lotions, shampoos, cleansers, colored makeup foundation, colored makeup powder, and colored makeup concealers.

2. Prior Art

Cosmetics have been in use since Biblical times. They served not only to soothe the skin and provide relief from minor irritations, but also to cover skin defects and to enhance beauty.

The physician's credo to "first, do no harm", however, is of considerable importance concerning skin care products. If aesthetic concerns were the only consideration with respect to cosmetics, another cosmetic line would certainly not be necessary.

However, potential problems exist with all cosmetics and skin care products currently on the market. Acne cosmetica is a problem seen all too frequently by the dermatologist. Comedogenicity is another major concern. Chemicals such as Isopropyl Myristate, Steareth 16, Isopropyl Palmitate, Cetyl Alcohol, Stearic Acid, Stearic Acid, Laureth-4, and many others are major causes of acne among users and yet are still found in many current cosmetic products. Oils or petroleum products such as mineral oil, Vitamin E, Jojoba oil or petrolatum cause severe acne in many patients. As a dermatologist and dermatologic surgeon I have spent the past 20 years treating the resultant acne scarring with chemical peeling, dermabrasion, dermal grafting, and laser surgery. I therefore have sought to invent a line of skin care products that would not initiate acne and hence, would protect patients from the need for correction of the disfiguring sequelae.

Many chemicals, though not comedogenic, frequently cause contact dermatitis. Indeed, many products on the market contain ingredients that are included in the North American Contact Dermatitis Society's standard patch test tray of 20 allergens. Products such as Cetyl Alcohol, Stearyl Alcohol, Lanolin (which aggravates eczema or atopic dermatitis), Propylene Glycol, Laureth-4, Steareth-16, Vitamin E, and other alcohols are frequent causes of contact dermatitis and irritant dermatitis. Imidazolidinyl urea and Quaternium-15 are releasers of formaldehyde, the chemical responsible for some of the most severe cases of contact dermatitis seen by a dermatologist. Fragrances, including Balsam of Peru, Cinammic Alcohol and Aldehyde and numerous natural plant products and extracts are the most common causes of contact dermatitis originating from cosmetics. Many patients also find perfumes offensive. No product can, of course, be "non-allergenic"—even water can cause a form of hives known as aquagenic urticaria.

However, it is possible to create a line that is as hypoallergenic as possible by avoiding the use of chemicals listed in the master list of comedogenic/irritating chemicals. Such a list has been detailed by James E. Fulton, Jr., M.D. and is entitled "Comedogenicity and Irritancy of Commonly Used Ingredients in Skin Care Products". (Journal of the Society of Cosmetic Chemists, Vol. 40, pps 321–333, November 1989).

One important point for discussion and consideration is the concentration of such comedogenic/irritating chemicals in the actual marketed products. Fulton, however, makes the key point that "The major offenders, such as Isopropyl Myristate, Acetylated Lanolin Alcohol and Lauric Acid derivatives such as Laureth-4 should be used with caution in skin care products. We are not convinced of the statement that lower concentrations of these compounds can be safely used with no comedogenic consequences. Human skin studies have been used to give that statement credence, but the back skin of human volunteers is relatively insensitive. However, when the rabbit ear assay is positive, but the human back skin results are negative after only 8 weeks exposure, the results from the rabbit ear assay should not be dismissed. The reaction may take longer or the back skin may not be the ideal testing substance."

Therefore, avoidance of such disease—aggravating compounds would seem to be a priority with cosmetic manufacturers. One frequently encounters claims of non-comedogenicity, non-irritancy and hypoallergenicity among cosmetic products currently on the shelf.

However, a quick review of the ingredient list from all currently marketed products always reveals one or more major offenders present on Fulton's list. It is quite possible that the test sample required for acnegenicity claims (25 patients) or allergenicity claims (50 to 200 patients) may be too small, however, to detect problems that we dermatologists frequently see among larger or more varied patient populations.

TABLE OF COMEDOGENICITY RATINGS AND IRRITANCY RATINGS AMONG COMMONLY USED COSMETIC INGREDIENTS

| COMPONENTS | COMEDOGENICITY RATING | IRRITANCY RATING |
|---|---|---|
| Petrolalum | 5 | 0 |
| Cetyl Alcohol | 2 | 2 |
| Stearic Acid | 2–3 | 0 |
| Stearyl Alcohol | 2 | 2 |
| Lanolin Products | 0–4 | 0–3 |
| Triethanolamine | 2 | 0 |
| Fragrance | 0 | 0–5+ |
| Imidazolidinyl urea | 0 | 0–5+ |
| Quaternium-15 (formaldehyde releasers) | 0 | 0–6+ |
| Propylene Glycol | 0 | 0–5+ |
| Laureth-4 | 4 | 4 |
| Steareth-16 | 5 | 1–3 |
| Isopropyl Myristate | 2–4 | 3 |
| Isopropyl Palmitate | 5 | 1 |
| Oils | 4 | 1–2 |
| Dyes | 1–3 | 1–2 |
| Vitamin-E | 0–3 | 0–3 |
| Comedogenic or Irritating Alcohols | 1–5 | 1–5 |

Why, then, has a line such as mine never been formulated? One consideration is the ready availability of inexpensive chemicals such as Petrolatum or Mineral Oil. Another factor is the tendency to repeat endlessly minor variations of older formulas in existence for many years. Additionally, larger manufacturers may simply be able to afford to ignore the 1% to 2% of patients who develop acne or contact dermatitis, reasoning that a refund may be expeditious from the business sense. Finally, the restriction of an ingredient formulary to items rated "0" on Fulton's list greatly reduces the chemicals still available for inclusion in such a cosmetic line.

The increasing world wide prevalence of skin cancer, (basal cell carcinoma, squamous cell carcinoma and malignant melanoma) has led many formulators to include sunscreens in skin care products applied to exposed areas. The formulator must seek to employ ingredients providing adequate sun protection while avoiding comedogenicity and irritancy.

Alpha-hydroxy acids have been included in many cosmetics in recent years. These "fruit acids" have been found in numerous studies to increase synthesis of dermal collagen, decrease signs of aging and sun damage (including rhytides and dyspigmentation) and to provide mild keratolysis and desquamation. However, the clinical effect of these acids is directly dependent upon the degree of buffering, and resultant pH, of the acid in the cosmetic. Many products sold over the counter contain glycolic or other acids in concentrations so low, or a pH so high, as to render these acids ineffective for the purpose for which they were added. It takes a fine balancing act, and many evaluations by an experienced dermatologist, to arrive at a glycolic acid concentration which minimizes stinging and burning and yet has a pH low enough, and a concentration high enough, to exert a long-term clinical effect.

As a practicing dermatologist and dermatologic surgeon I feel that it is essential to design a product line that contains effective concentrations of pertinent chemicals while avoiding components known to be allergenic, irritating, acne causing, or comedogenic. Such a cosmetic line would prove to be aesthetically pleasing and yet avoid common clinical problems such as acne scarring, irritant dermatitis, photosensitivity, or permanent allergic contact sensitization.

SUMMARY

Accordingly, it is an object of the present invention to overcome the aforementioned disadvantages of the prior art.

It is another object of the invention to develop a line of cosmetics that is oil free, fragrance free, lanolin free and free of formaldehyde releasing preservatives.

It is still another object of the invention to provide a line of cosmetics that is hypoallergenic, noncomedogenic and nonacnegenic.

It is still another object of the invention to provide a line of cosmetics that contains only those ingredients rated "0" on the master published list of cosmetic comedogenicity and irritancy.

It is still another object of the invention to provide a moisture cream that is soothing, aesthetically pleasing, possesses all of the above-mentioned qualities, and contains the ingredients Emulsifying Wax, C12–15 Alkyl Benzoate, Behenic Acid, Cetyl Palmitate, Sodium PCA, Allantoin, Sorbitan Sequioleate, Hyaluronic Acid Gel, Polysorbate 20, Methylparaben, Propylparaben, distilled water, and possibly other ingredients.

It is still another object of the invention to provide a moisture cream that is hypoallergenic, nonacnegenic, noncomedogenic, oil free, fragrance free, lanolin free, free of formaldehyde releasing preservatives and with all ingredients rated "0" on Fulton's list with respect to comedogenicity and irritancy.

It is still another object of the invention to provide a moisture lotion that contains the ingredients Emulsifying Wax, C12–15 Alkyl Benzoate, Sodium PCA, Behenic Acid, Cetyl Palmitate, Allantoin, Sorbitan Sesquioleate, Sodium Carboxymethylcellulose, Hyaluronic Acid Gel, Polysorbate 20, Methylparaben, Propylparaben, and distilled water.

It is still another object of the invention to provide a moisture lotion that is hypoallergenic, nonacnegenic, noncomedogenic, oil free, fragrance free, lanolin free, free of formaldehyde releasing preservatives and with all ingredients rated "0" on Fulton's list with respect to comedogenicity and irritancy.

It is still another object of the invention to provide a glycolic acid containing moisture cream that contains the ingredients Glycolic Acid 70%, distilled water, Sodium Hydroxide, Emulsifying Wax, C12–15 Aklyl Benzoate, Behenic Acid, Cetyl Palmitate, Sodium PCA Allantoin, Sorbitan Sesquioleate, Hyaluronic Acid Gel, Polysorbate 20, Methylparaben, Propylparaben, and distilled water.

It is still another object of the invention to provide a glycolic acid containing moisture cream that is hypoallergenic, nonacnegenic, noncomedogenic, oil free, fragrance free, lanolin free, free of formaldehyde releasing preservatives and with all ingredients rated "0" on Fulton's list with respect to comedogenicity and irritancy.

It is still another object of the invention to provide a glycolic acid containing moisture lotion that contains the ingredients Glycolic Acid 70%, distilled water, Sodium Hydroxide Emulsifying Wax, C12–15 Aklyl Benzoate, Sodium PCA, Behenic Acid, Cetyl Palmitate, Allantoin, Sorbitan Sesquioleate, Sodium Carboxymethycellulose Hyaluronic Acid Gel, Polysorbate 20, Methylparaben, Propylparaben, distilled water and possibly other ingredients.

It is still another object of the invention to provide a glycolic acid containing moisture lotion that is hypoallergenic, nonacnegenic, noncomedogenic, oil free, fragrance free, lanolin free, free of formaldehyde releasing preservatives and with all ingredients rated "0" on Fulton's list with respect to comedogenicity and irritancy.

It is still another object of the invention to provide a shampoo that contains the ingredients Alkyl Polyglucoside and Ammonium Laureth Sulfate, Glycerin, Ammonium Chloride, Dimethicone, Hydrolyzed Wheat Protein, Citric Acid, Methylparaben, Propylparaben, and distilled water.

It is still another object of the invention to provide a shampoo that is hypoallergenic, nonacnegenic, noncomedogenic, oil free, fragrance free, lanolin free, free of formaldehyde releasing preservatives and with all ingredients rated "0" on Fulton's list with respect to comedogenicity and irritancy.

It is still another object of the invention to provide a cleanser that contains the ingredients Emulsifying Wax, Alkyl Polyglucoside and Ammonium Laureth Sulfate, Methylparaben, Propylparaben, and distilled water. It is still another object of the invention to provide a cleanser that is hypoallergenic, nonacnegenic, noncomedogenic, oil free, fragrance free, lanolin free, free of formaldehyde releasing preservatives and with all ingredients rated "0" on Fulton's list with respect to comedogenicity and irritancy.

It is still further object of the invention to provide a makeup foundation line, in various skin colors, that contains the ingredients Deionized Water, Magnesium Aluminum Silicate, Cellulose Gum, Glycerin, Sorbitol, Phenoxyethanol, Methylparaben, Butylparaben, Ethylparaben, and Propylparaben Polysorbate 20, Titanium Dioxide, Lecithin, Kaolin, various iron oxides, Steareth-100, Octyldodecyl Stearoyl Stearate, Diisopropyl Adipate, Behenic Acid, Glycerol Stearate, Cetyl Palmitate, Choleth-24, PEG-5 Soya Sterol, Octyl Methoxycinnimate, Aminomethyl Propanol, Panthenol and also possibly combinations of Magnesium Aluminum Silicate, Cellulose Gum, Glycerin, Sorbitol, Phenoxyethanol and Methylparaben, Butylparaben, Ethylparaben and Propylparaben, Polysorbate-20, Titanium Dioxide, Kaolin, various iron oxides, Steareth-100, Octyldodecyl Stearoyl Stearate, Diisopropyl Adipate, Behenic Acid, Cyclomethicone, Cetyl Palmitate, Choleth-24, PEG-5 Soya Sterol, Octyl Methoxycinnimate, Aminomethyl Propanol, and Panthenol and possibly other ingredients.

It is a further object of the invention to provide a makeup foundation line, in various skin colors, that is hypoallergenic, nonacnegenic, noncomedogenic, oil free, fragrance free, lanolin free, free of formaldehyde releasing preservatives and with all ingredients rated "0" on Fulton's list with respect to comedogenicity and irritancy.

It is still further object of the invention to provide a makeup powder line, in compact or powder form, in various skin colors, that contains the ingredients Talc, Kaolin, Zinc Stearate, Octyldodecyl Stearoyl Stearate, Diisopropyl Adipate, Methylparaben, Propylparaben and various shades of Titanium Dioxide, Iron Oxides and Ultramarine Blue.

It is still a further object of the invention to provide a makeup powder line in compact or powder form in various skin colors, that is hypoallergenic, nonacnegenic, noncomedogenic, oil free, fragrance free, lanolin free, free of formaldehyde releasing preservatives and with all ingredients rated "0" on Fulton's list with respect to comedogenicity and irritancy.

It is still further object of the invention to provide a makeup concealer line, in stick form or in a small pot or jar, in various skin colors, that contains the ingredients Octyldodecyl Stearoyl Stearate, Diisopropyl Adipate, Octyl Methoxycinnimate, Cetyl Palmitate, Behenic Acid, Methylparaben, Tribehenin, Propyyparaben, Ceresin Waxes, Titanium Dioxide and Lecithin, Bentonite, and various Iron Oxides as well as Tocopherol Acetate and possibly other ingredients.

It is still a further object of the invention to provide a makeup concealer line in stick form in a pot or jar in various skin colors, that is hypoallergenic, nonacnegenic, noncomedogenic, oil free, fragrance free, lanolin free, free of formaldehyde releasing preservatives and with all ingredients rated "0" on Fulton's list with respect to comedogenicity and irritancy.

Additional objects, advantages, and novel features of the invention will be set forth in part in the description which follows, and in part will become apparent to those skilled in the art on examination of the following, or may be learned by practice of the invention.

DESCRIPTION OF THE MANUFACTURE

For the manufacture of the moisturizing cream the Emulsifying Wax, Cetyl Palmitate and Behenic Acid are mixed and melted at approximately 65 degrees C. The Parabens, C12–15 Alkylbenzoate, Sorbitan Sesquioleate and Polysorbate 20 are added to the above mentioned mixture.

Distilled water is then warmed. Allantoin is dissolved into this distilled water after heating it to approximately 60 degrees C.

The oil phase is then blended into the water phase and mixed to cool. The SodiumPCA and Hyaluronic Acid Gel are then blended into the resultant mixture. For best results the final product should be homogenized.

The moisturizing lotion is made with the following technique: The Emulsifying Wax, Cetyl Palmitate, and Behenic Acid are melted at approximately 65 degrees C. To this mixture are added Parabens, C12–15 Aklyl Benzoate, Sorbitan Sesquioleate, and Polysorbate 20.

Distilled water is then warmed. Allantoin is dissolved into the distilled water after heating it to approximately 60 degrees C.

Sodium Carboxymethylcellulose is added to the water phase and mixed until gelling occurs.

The oil phase is then added to the water phase and mixed until cooling occurs.

SodiumPCA and Hyaluronic Acid Gel are then blended. For best results the final product should be homogenized.

The Glycolic Acid Cream is manufactured as follows: A stock solution of Glycolic Acid solution is prepared by mixing Glycolic Acid 70%, distilled water, and Sodium Hydroxide until the desired pH has been obtained. Next the Emulsifying Wax, Cetyl Palmitate and Behenic Acid are melted and mixed at approximately 65 degrees C. To this mixture is added Parabens, C12–15 Alkyl Benzoate, Sorbitan Sesquioleate and Polysorbate 20.

The Glycolic Acid stock solution is then added to distilled water. Allantoin is dissolved into this mixture of distilled water and Glycolic Acid by heating it to approximately 60 degrees C. The oil phase is then blended into the water phase and mixed until cooling occurs. The SodiumPCA and Hyaluronic Acid Gel are then blended into the resultant mixture. For best results the final product should be homogenized.

For the Glycolic Lotion a similar above-mentioned Glycolic Acid Stock Solution is prepared. Next the Emulsifying Wax, Cetyl Palmitate, and Behenic Acid are melted and mixed at approximately 65 degrees C. The Parabens, C12–15 Alkyl Benzoate, Sorbitan Sesquioleate and Polysorbate 20 are added to this mixture.

The Glycolic Acid stock solution is added to distilled water. Allantoin is dissolved into this mixture by heating it to approximately 60 degrees C. Sodium Carboxymethylcellulose is added to this water phase and mixed until gelling occurs. The oil phase is blended into the water phase and mixed until cooling occurs. Next SodiumPCA and Hyaluronic Acid Gel are mixed into the final mixture. For best results the final product should be homogenized.

The shampoo is manufactured by the following technique: One must first wet the Parabens with Glycerin and dissolve these two compounds into Aklyl Polyglucoside and Ammonium Laureth Sulfate, heating the mixture to approximately 50 degrees C. The Citric Acid and Ammonium Chloride are mixed into distilled water at approximately 50 degrees C. These two mixtures are blended with light stirring until they have cooled. Finally the Dimethicone and Hydrolyzed Wheat Protein are added to the final mixture.

The cleanser is manufactured as follows: The Emulsifying Wax is melted to approximately 50 degrees C. Parabens are added to this mixture. Distilled water is then warmed to 45 to 50 degrees C. These two phases are blended until homogenous. Alkyl Polyglucoside and Ammonium Laureth Sulfate are warmed to 45 to 50 degrees C. and stirred into the emulsion very lightly (to prevent induction of foam) until they are cool.

The liquid makeup is manufactured as follows: The water is heated to 85 degrees C. (phase A). The Cellulose Gum and Magnesium Aluminum Silicate are disbursed in Glycerin and Sorbitol, and added to the water with a high speed homomixer agitation (phase B). They are mixed for 15 minutes at 85 degrees C. Then, slowly is added the Phenoxyethanol, Methylparaben, Butylparaben, Ethylparaben and Propylparaben mixture with moderate homomixer agitation and this is mixed for 3 minutes at 85 degrees.

Tween 80 is also included in this phase.

Next the pigments, (phase C) including Titanium Dioxide and Iron Oxides as well as Lecithin and Kaolin are added to the above phases A and B at 85 degrees C. with high speed homomixer agitation. These are agitated for 30 minutes. The tank lid is kept closed to avoid water loss.

The Steareth-100 (phase D) is then added to the above three phases with slow speed homomixer agitation. They are mixed until homogeneous for about 3 to 5 minutes.

The next phase E is mixed including: Octyldodecyl Stearoyl Stearate, Diisopropyl Adipate, Behenic Acid, Gylceryl Stearate, PEG100 Stearate, Cetyl Palmitate, Choleth-24, PEG-5 Soya Sterol and Octyl Methoxycinnimate are heated to 85 degrees C. with slow propeller agitation. This phase is added to the above 4 phases with slow speed homomixer agitation for 5 to 10 minutes until homogeneous. Next the Aminomethyl Propanol is added and agitated with moderate propeller agitation for 5 to 10 minutes at 85 degrees C. until homogeneous. Forced cooling is then commenced with moderate propeller agitation to 40 to 45 degrees C. Finally Panthenol is added to the batch at 40 degrees C. and cooled to room temperature with moderate propeller agitation.

Alternatively the liquid makeup may be made as follows: The water is heated to 85 degrees C. The Cellulose Gum and Magnesium Aluminum Silicate and Glycerin and Sorbitol are added to the water with high speed homomixer agitation and mixed for 15 minutes. The remaining preservatives (Phenoxyethanol, Methylparaben, Butylparaben, Ethylparaben and Propylparaben) are added to the above phase with moderate homomixer agitation and mixed for 3 to 5 minutes at 85 degrees C. Then, slowly is added Polysorbate-20 which is again mixed for 3 minutes at 85 degrees C.

To the above mixture is added the Titanium Dioxide, Kaolin and Iron Oxides at 85 degrees C. with high speed homomixer agitation. This mixture is agitated for 30 minutes. The tank lid is kept closed to avoid water loss.

Next Steareth-100 is added to the above mixture with slow speed homomixer agitation and mixed until homogeneous for about 3 to 5 minutes. The Octyldodecyl Stearoyl Stearate, Diisopropyl Adipate, Behenic Acid, Cyclomethicone, Cetyl Palmitate, Choleth-24, PEG-5 Soya Sterol and Methoxycinnimate are combined to the above mixture and heated to 85 degrees C. with slow propeller agitation. With the mixture at 85 degrees C., the combination is mixed until homogeneous. Finally, Aminomethyl Propanol is added and agitated with moderate propeller agitation for 5 to 10 minutes at 85 degrees C. until homogenous. Then forced cooling is begin with moderate propeller agitation at 40 to 45 degrees C. Finally Panthenol is added to the batch at 40 degrees C. and cooled to room temperature with moderate propeller agitation.

For manufacture of the pressed face powder, the Talc, Kaolin and Zinc Stearate are combined. Next Octyldodecyl Stearoyl Stearate and Diisopropyl Adipate are added along with Methylparaben and Propylparaben and mixed at the appropriate temperature until the desired consistency has been obtained.

To manufacture the concealer, in a stainless steel jacketed tank, the Octyldodecyl Stearoyl Stearate, Diisopropyl Adipate, Octyl Methoxycinnimate, Cetyl Palmitate, Behenic Acid, Methylparaben, Tribehenin, Propylparaben and Ceresin Waxes are combined and heated to 80 to 85 degrees C. with moderate propeller agitation. They are mixed at 80 to 85 degrees C. with propeller agitation until all waxes are melted and then held at 80 degrees C. with gentle agitation for 20 minutes at 75 to 80 degrees C.

Next are mixed and combined the Titanium Dioxide, Lecithin, Kaolin and Iron Oxides. They are added to the above phase at 85 degrees C. with high speed homomixer (Silverson) agitation at 5500 to 6500 rpm. The mix dries with homomixer agitation at 75 degrees C. for one hour. Dispersion is checked on a Hegeman gauge and if necessary, the batch is passed through a 3-roll mill. Next the Tocopherol Acetate is added to the batch at 70 to 75 degrees C. with slow propeller agitation. It is mixed until homogeneous for about 10 minutes. Samples are pulled and added for shade evaluation.

The above discussion of this invention is directed primarily to preferred embodiments and practices thereof. It will be readily apparent to those skilled in the art that further changes and modifications in the actual implementation of the concepts described herein can readily be made without departing from the spirit and scope of the invention as defined by the following claims.

I claim:

1. A hypoallergenic, noncomedogenic, nonacnegenic cosmetic composition which is oil free, lanolin free, fragrance free and free of formaldehyde releasing preservative, the composition containing only ingredients rated 0 with respect to comedogenicity and irritancy.

2. The composition of claim 1 which is a moisturizing cream.

3. The moisturizing cream of claim 2 which comprises emulsifying wax, cetyl palmitate, behenic acid, methylparaben, propylparaben, C12–15 alkylbenzoate, sorbitan sesquioleate, polysorbate 20, allantoin, sodium PCA, hyaluronic acid gel, and distilled water.

4. The composition of claim 1 which is a moisturizing lotion.

5. The moisturizing lotion of claim 4 which comprises emulsifying wax, cetyl palmitate, behenic acid, methylparaben, propylparaben, C12–15 alkylbenzoate, sorbitan sesquioleate, polysorbate 20, allantoin, sodium carboxymethylcellulose, sodium PCA, hyaluronic acid gel, and distilled water.

6. The composition of claim 1 which contains an alpha-hydroxy acid.

7. The composition of claim 6 wherein the alpha-hydroxy acid is glycolic acid.

8. The composition of claim 6 or 7 which is a cream.

9. The cream of claim 8 which comprises sodium hydroxide, emulsifying wax, cetyl palmitate, behenic acid, methylparaben, propylparaben, C12–15 alkylbenzoate, sorbitan sesquioleate, polysorbate 20, allantoin, sodium PCA, hyaluronic acid gel, and distilled water.

10. The composition of claim 6 or 7 which is a lotion.

11. The lotion of claim 10 which comprises sodium hydroxide, emulsifying wax, cetyl palmitate, behenic acid, methylparaben, propylparaben, C12–15 alkylbenzoate, sorbitan sesquioleate, polysorbate, allantoin, sodium carboxymethylcellulose, sodiumPCA, hyaluronic acid gel, and distilled water.

12. The composition of claim 1 which is a shampoo.

13. The shampoo of claim 12 which comprises methylparaben, propylparaben, glycerin, alkyl polyglucoside, ammonium laureth sulfate, citric acid, ammonium chloride, dimethicone, hydrolyzed wheat protein and distilled water.

14. The composition of claim 1 which is a cleanser.

15. The cleanser of claim 14 which comprises emulsifying wax, methylparaben, propylparaben, alkyl polyglucoside, ammonium laureth sulfate and distilled water.

16. The composition of claim 1 which is a colored makeup product.

17. The makeup product of claim 16 which is a liquid foundation.

18. The foundation of claim 17 which comprises cellulose gum, magnesium aluminum silicate, glycerin, sorbitol, phenoxyethanol, methylparaben, butylparaben, ethylparaben, propylparaben, Tween 80, titanium dioxide, iron oxides, lecithin, kaolin, steareth 100, octyldodecylstearoyl stearate, diisopropyl adipate, behenic acid, glyceryl stearate, PEG100 stearate, cetyl palmitate, choleth-24, PEG5 soya sterol, octyl methoxycinnimate, aminomethyl propanol, panthenol, and deionized water.

19. The foundation of claim 18 which comprises cellulose gum, magnesium aluminum silicate, glycerin, sorbitol, phenoxyethanol, methylparaben, butylparaben, ethylparaben, propylparaben, polysorbate 20, titanium dioxide, iron oxides, kaolin, steareth 100, octyldodecylstearoyl stearate, diisopropyl adipate, behenic acid, cyclomethicone, cetyl palmitate, choleth-24, PEG5 soya sterol, octyl methoxycinnimate, aminomethyl propanol, panthenol, and deionized water.

20. The makeup product of claim 16 which is a powder.

21. The powder of claim 20 which comprises talc, kaolin, zinc stearate, octyldodecylstearoyl stearate, diisopropyl adipate, methylparaben, propylparaben, titanium dioxide, iron oxides and ultramarine blue.

22. The makeup product of claim 16 which is a concealer.

23. The concealer of claim 22 which comprises octyldodecylstearoyl stearate, diisopropyl adipate, octyl methoxycinnimate, cetyl palmitate, behenic acid, methylparaben, tribehenin, propylparaben, ceresin waxes, titanium dioxide, lecithin, kaolin, iron oxides, and tocopherol acetate.

24. A method of making a hypoallergenic, noncomedogenic, nonacnegenic cosmetic composition which is oil free, lanolin free, fragrance free and free of formaldehyde releasing preservative, the method comprising combining only ingredients rated 0 with respect to comedogenicity and irritancy so as to form the composition.

\* \* \* \* \*